US012629108B2

(12) United States Patent
Beacham et al.

(10) Patent No.: US 12,629,108 B2
(45) Date of Patent: May 19, 2026

(54) SELF CONTAINED CT SCINTILLATORS WITHIN A 3-D PRINTED COLLIMATOR FIELD

(71) Applicant: GE Precision Healthcare LLC, Waukesha, WI (US)

(72) Inventors: Jimmie Beacham, West Allis, WI (US); Jaroslaw Kurzac, Oconomowoc, WI (US); Kevin David, Pewaukee, WI (US)

(73) Assignee: GE Precision Healthcare LLC, Waukesha, WI (US)

( * ) Notice: Subject to any disclaimer, the term of this patent is extended or adjusted under 35 U.S.C. 154(b) by 266 days.

(21) Appl. No.: 18/458,791

(22) Filed: Aug. 30, 2023

(65) Prior Publication Data

US 2025/0072843 A1     Mar. 6, 2025

(51) Int. Cl.
*A61B 6/03*          (2006.01)
*B28B 1/00*          (2006.01)
(Continued)

(52) U.S. Cl.
CPC .............. *A61B 6/032* (2013.01); *B28B 1/001* (2013.01); *B33Y 80/00* (2014.12); *B33Y 40/20* (2020.01); *B33Y 70/00* (2014.12)

(58) Field of Classification Search
CPC ........... A61B 6/032; A61B 6/06; A61B 6/035; A61B 6/40; A61B 6/4208; A61B 6/54; B28B 1/001; B33Y 80/00; B33Y 40/20; B33Y 70/00; B33Y 30/00; G01T 1/20183; G01T 1/2985; G01T 1/2002; B22F 12/00; B29C 64/141
See application file for complete search history.

(56) References Cited

U.S. PATENT DOCUMENTS 5,012,103 A * 4/1991 Tanaka ................... G01T 1/2002
                                                    250/361 R
7,112,797 B2     9/2006 Hoge
(Continued)

FOREIGN PATENT DOCUMENTS

| JP | H1036833 A | 2/1998 |
| KR | 20220005196 A | 1/2022 |
| WO | 2022010199 A1 | 1/2022 |

OTHER PUBLICATIONS

EP application 24194146.7 filed Aug. 12, 2024—extended Search Report issued Jan. 13, 2025; 7 pages.
(Continued)

*Primary Examiner* — Courtney D Thomas

(57)                ABSTRACT

Post-patient collimators and methods of manufacturing post-patient collimators are provided. An example method includes additively manufacturing a collimator array having a plurality of tapered cavities, positioning a plurality of scintillator pixels within the tapered cavities of the collimator array, and hardening the pixels within the tapered cavities. An example post-patient collimator includes a collimator array including a plurality of cavities, wherein each of the plurality of cavities includes tapered walls, a scintillator including a plurality of pixels, each of the plurality of pixels positioned with one of the plurality of cavities of the collimator, and a reflector positioned on a top of each of the plurality of pixels.

19 Claims, 7 Drawing Sheets

(51) Int. Cl.
 _B33Y 80/00_ (2015.01)
 _B33Y 40/20_ (2020.01)
 _B33Y 70/00_ (2020.01)

(56) References Cited

U.S. PATENT DOCUMENTS

| 10,408,947 | B2 | 9/2019 | Beacham |
| 2017/0329022 | A1* | 11/2017 | Bures ................. C09K 11/7719 |
| 2021/0080597 | A1 | 3/2021 | Wimmers |

OTHER PUBLICATIONS

WO2022010199 English Translation; 18 pages.
JP application 2024-133709 filed Aug. 9, 2024—Office Action issued Oct. 1, 2025; Machine Translation; 6 pages.
JPH10-36833 English Abstract; Espacenet.com Dec. 29, 2025; 1 page.
KR 2022-0005196 English Abstract; Espacenet.com Dec. 29, 2025; 1 page.

* cited by examiner

SELF CONTAINED CT SCINTILLATORS WITHIN A 3-D PRINTED COLLIMATOR FIELD

FIELD

Embodiments of the subject matter disclosed herein relate to diagnostic medical imaging, and more particularly, to computed tomography imaging setup with a post-patient collimator.

BACKGROUND

X-ray radiation detectors, such detectors used in CT imaging systems, include post-patient collimator assemblies having a collimator and a scintillator. Typically, existing post-patient collimator assemblies are separate components which may be attached to one another (e.g., a collimator positioned on top of the scintillator, or between the X-ray radiation source and the scintillator). The post-patient collimator assembly may be coupled to a photodiode to acquire data relating to the patient or subject being scanned with the CT imaging system to enable image reproduction.

SUMMARY

In one embodiment, a post-patient collimator for x-ray radiation includes a collimator array including a plurality of cavities, where each of the plurality of cavities includes tapered walls. The collimator array is additively manufactured. A scintillator includes a plurality of pixels, each positioned with one of the plurality of cavities of the collimator. A reflector positioned on a top of each of the plurality of pixels.

In another embodiment, a method of making a post-patient collimator for x-ray radiation includes additively manufacturing a collimator array having a plurality of tapered cavities, positioning a plurality of scintillator pixels within the collimator array, where each of the plurality of pixels is positioned in one of the plurality of tapered cavities, and hardening the pixels within the tapered cavities.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Figure 1:
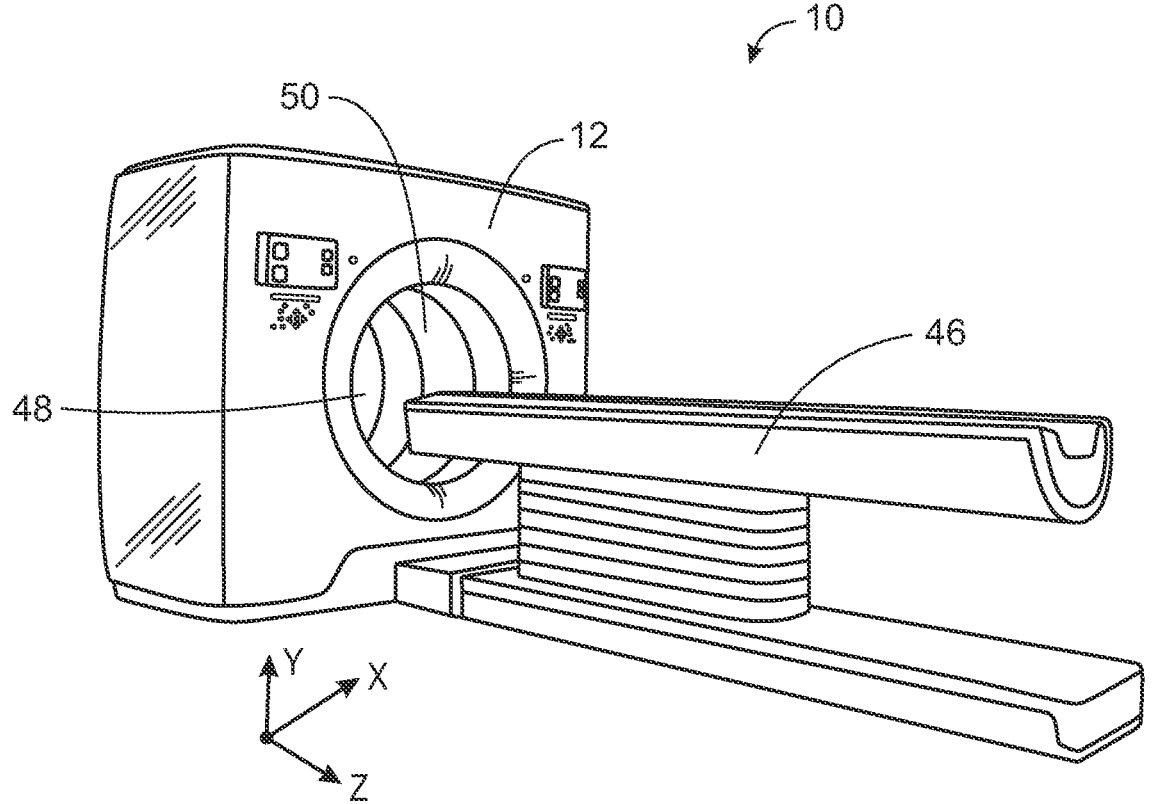
FIG. 1 shows a pictorial view of an imaging system according to an embodiment of the invention.
Figure 2:
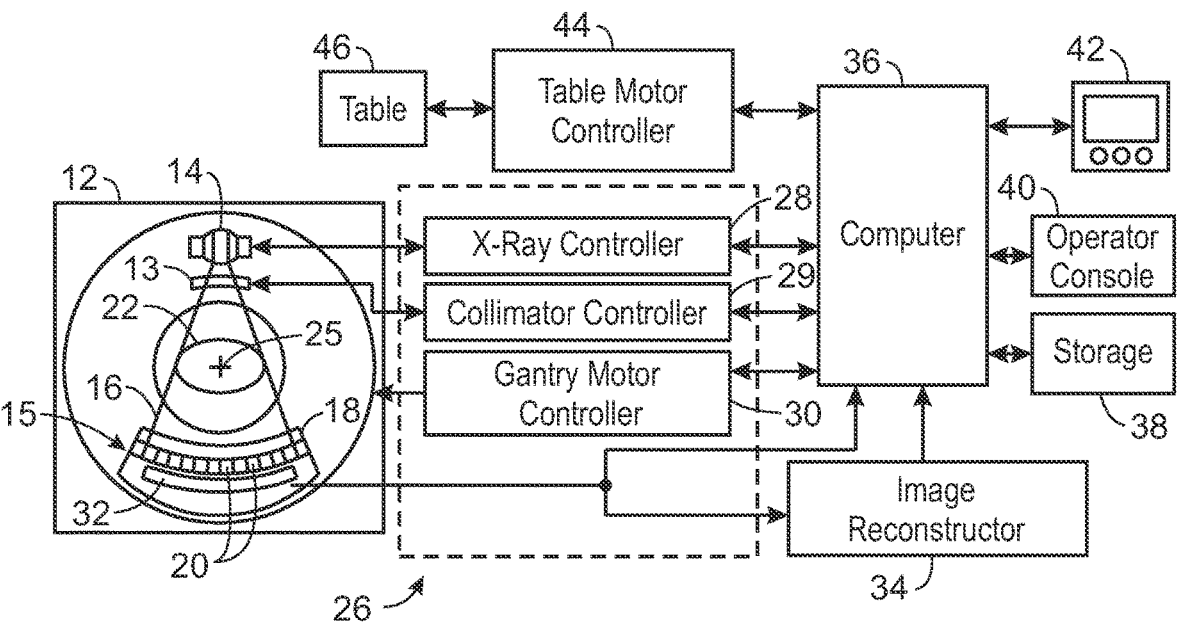
FIG. 2 shows a block schematic diagram of an exemplary imaging system according to an embodiment of the invention.
Figure 3:
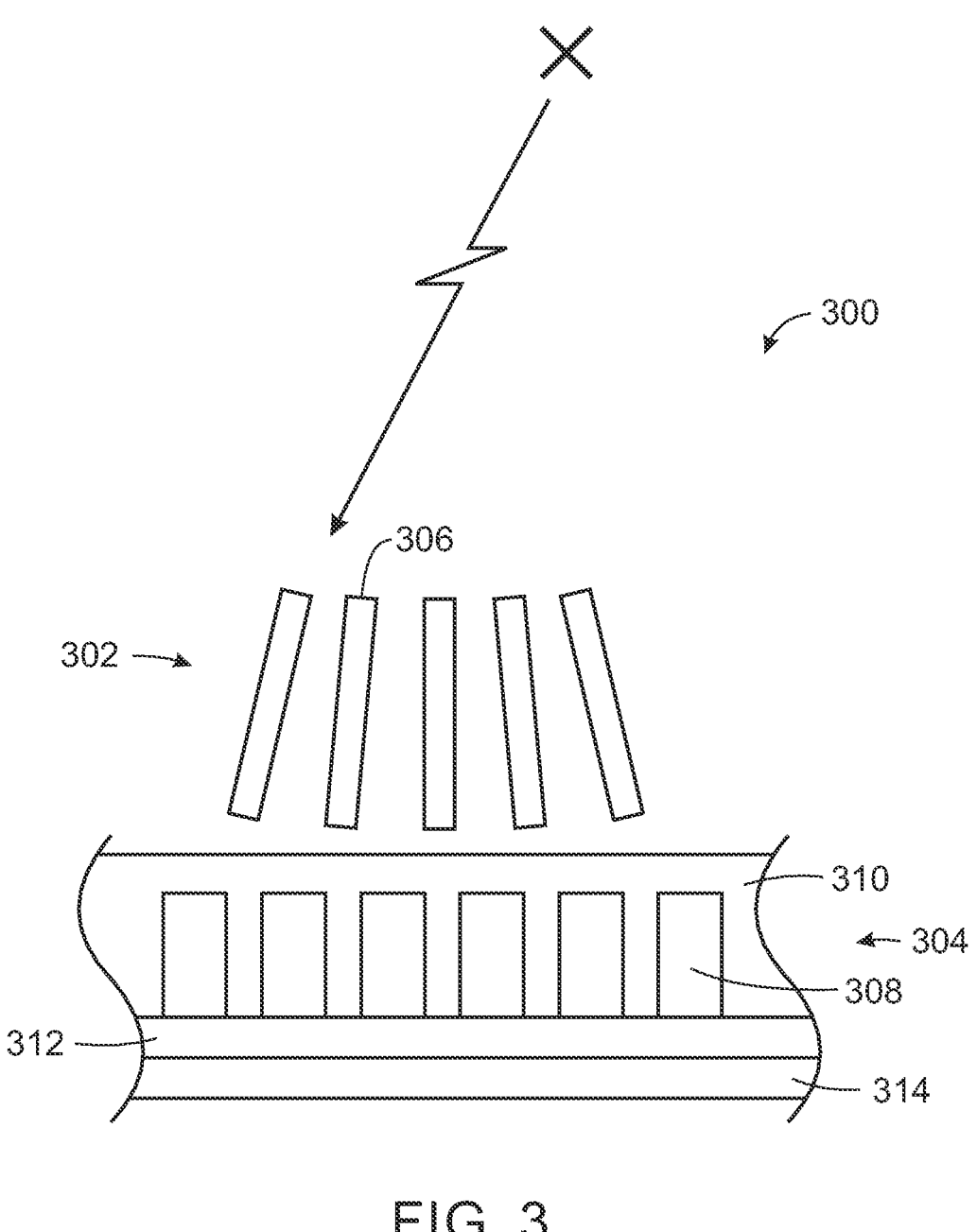
FIG. 3 depicts a current version of a post-patient collimator assembly including a collimator and a scintillator.
Figure 5:
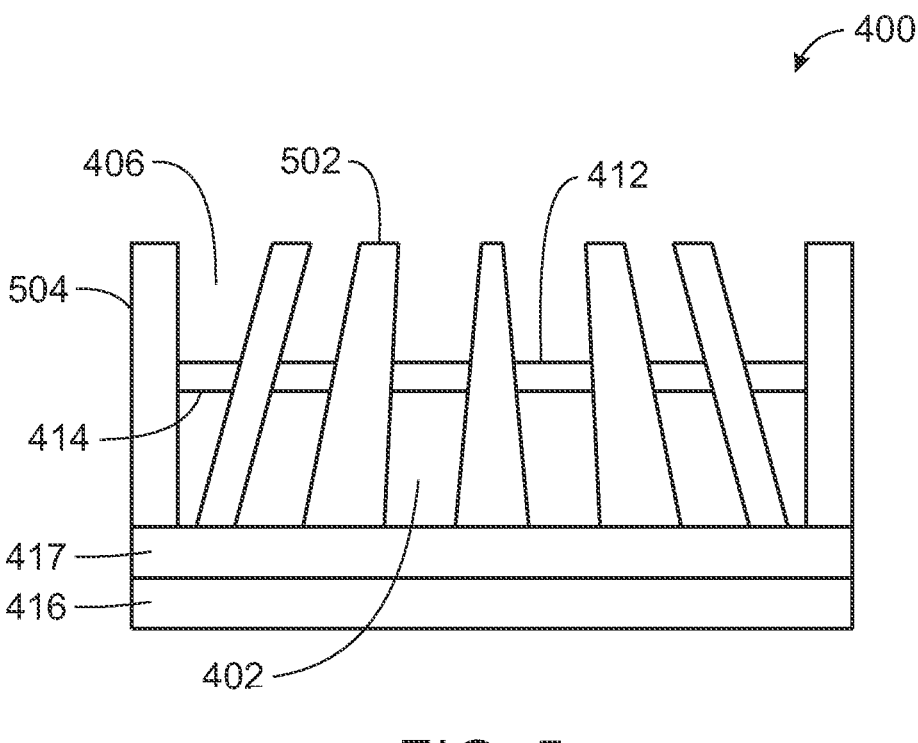
FIG. 5 depicts a cross-sectional view of the example post-patient collimator assembly depicted in FIGS. 4A-4G.
Figure 7:
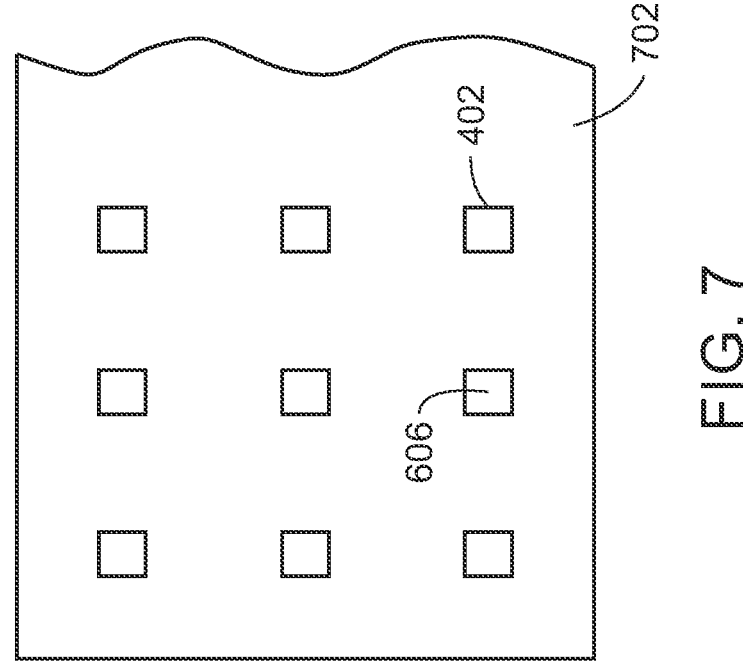
FIG. 7 depicts a bottom view of the example post-patient collimator assembly depicted in FIGS. 4A-6.
Figure 6:
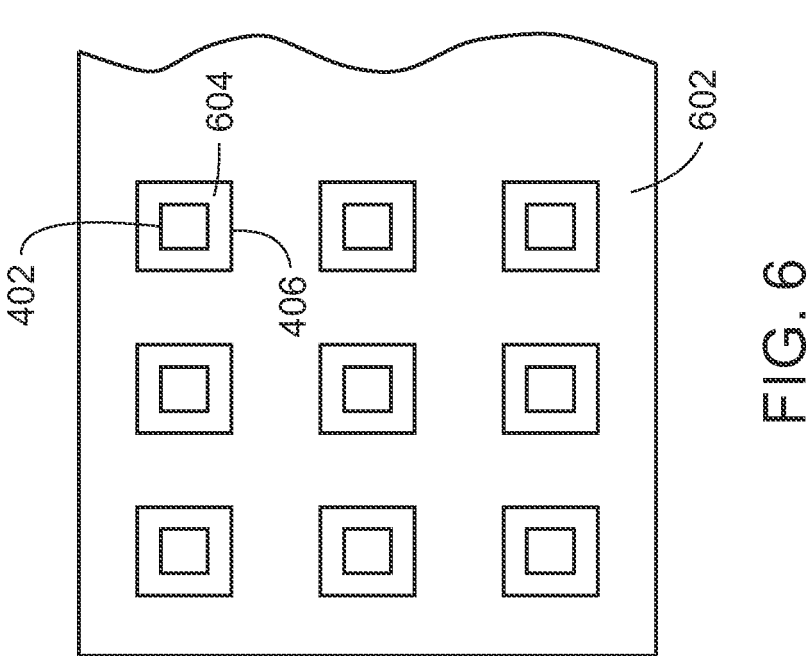
FIG. 6 depicts a top view of the example post-patient collimator assembly depicted in FIGS. 4A-5.
Figure 8:
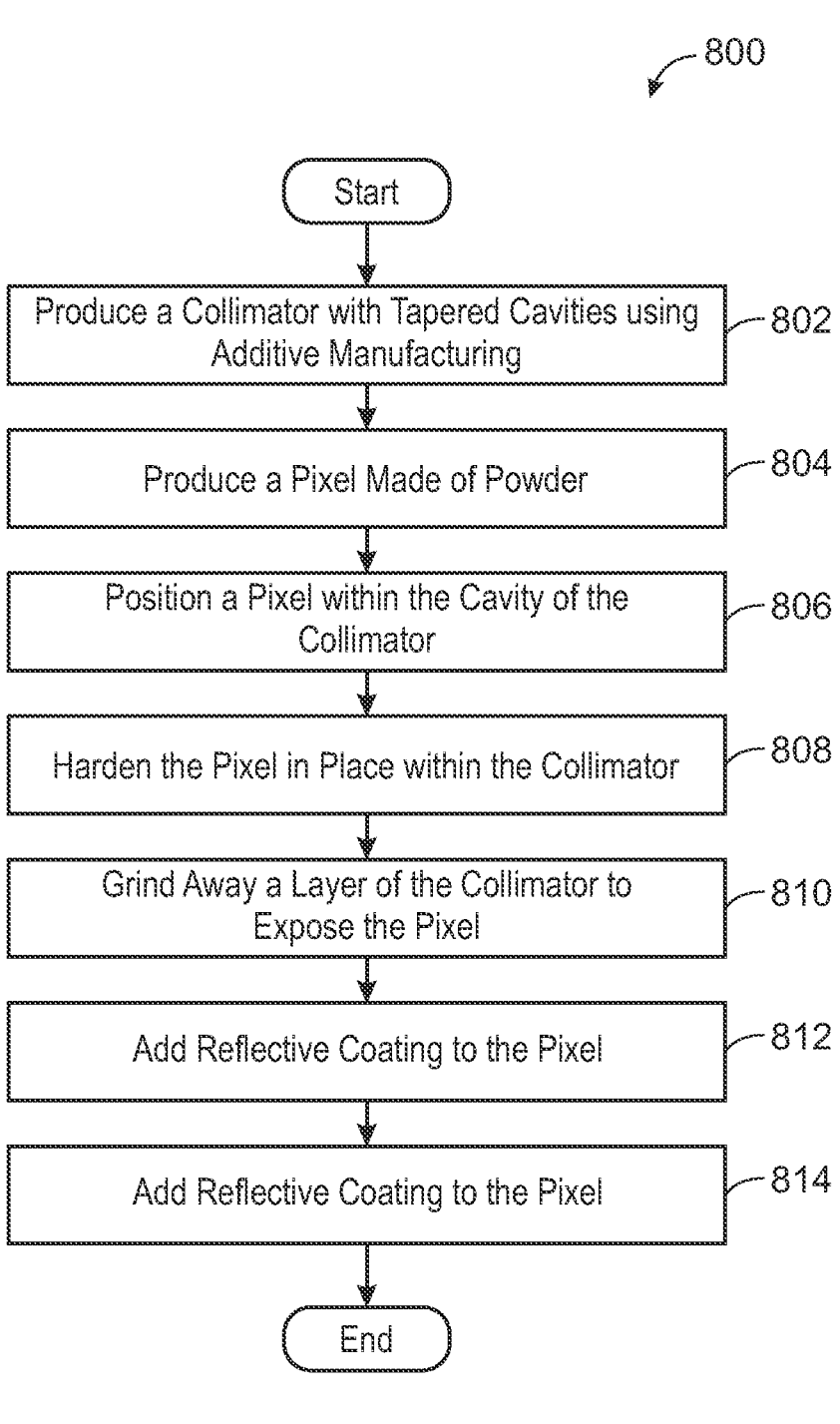
FIG. 8 an example method of manufacturing the post-patient collimator assembly depicted in FIGS. 4A-7.

The following description relates to various embodiments of x-ray imaging of a subject. In particular, systems and methods are provided for CT imaging using a post-patient collimator assembly, which includes a collimator and a scintillator. FIGS. 1-2 show an example embodiment of an imaging system including the post-patient collimator assembly positioned between the patient or subject and the detector. FIG. 3 depicts an example of a prior art post-patient collimator assembly in which the collimator is positioned between the X-ray source and the scintillator. In particular, the collimator is stacked on a top surface of the scintillator. FIGS. 4A-4G depict an example manufacturing process for a collimator assembly described herein, in which the collimator and scintillator are integrated. FIGS. 5-7 depict an example post-patient collimator assembly described herein, which may be manufactured using the manufacturing process depicted in FIGS. 4A-4G. FIG. 8 is a flowchart depicting an example method of manufacturing the post-patient collimator of FIGS. 5-7.

Though a CT system is described by way of example, it should be understood that the present techniques may also be useful when applied to images acquired using other imaging modalities, such as tomosynthesis, C-arm angiography, and so forth. The present discussion of a CT imaging modality is provided merely as an example of one suitable imaging modality.

Various embodiments may be implemented in connection with different types of imaging systems. For example, various embodiments may be implemented in connection with a CT imaging system in which a radiation source projects a fan- or cone-shaped beam that is collimated to lie within an x-y plane of a Cartesian coordinate system and generally referred to as an "imaging plane." The x-ray beam passes through an imaging subject, such as a patient. The beam, after being attenuated by the imaging subject, impinges upon an array of radiation detectors. The intensity of the attenuated radiation beam received at the detector array is dependent upon the attenuation of an x-ray beam by the imaging subject. Each detector element of the array produces a separate electrical signal that is a measurement of the beam intensity at the detector location. The intensity measurements from all the detectors are acquired separately to produce a transmission profile.

In third-generation CT systems, the radiation source and the detector array are rotated with a gantry within the imaging plane and around an object (such as a region of the subject) to be imaged such that the angle at which the x-ray beam intersects the imaging subject constantly changes. A complete gantry rotation occurs when the gantry concludes one full 360 degree revolution. A group of x-ray attenuation measurements (e.g., projection data) from the detector array at one gantry angle is referred to as a "view." A view is, therefore, each incremental position of the gantry. A "scan" of the object comprises a set of views made at different gantry angles, or view angles, during one revolution of the x-ray source and detector. In an axial diagnostic scan, the projection data is processed to construct an image that corresponds to a two-dimensional slice taken through the imaging subject. A scout scan (also referred herein as localizer scan) provides a projection view along a longitudinal axis of the imaging subject and generally provides aggregations each including internal structures of the subject. One method for reconstructing an image from a set of projection data is referred to in the art as a filtered back-projection technique. This process converts the attenuation measurements from a scan into integers called "CT numbers" or "Hounsfield units" (HU), which are used to control the brightness of a corresponding pixel on a display.

FIG. 1 illustrates an exemplary computed tomography (CT) imaging system 10 and FIG. 2 depicts an example block diagram of the exemplary imaging system according to an embodiment of the invention. The CT imaging system includes a gantry 12. The gantry 12 has an X-ray source 14 that generates and projects a beam of X-rays 16 toward a detector assembly 15 on the opposite side of the gantry 12. The X-ray source 14 projects the beam of X-rays 16 through a pre-patient collimator assembly 13 that determines the size and shape of the beam of X-rays 16 using, for example, one or more filters. The detector assembly 15 includes a collimator assembly 18 (a post-patient collimator assembly), a plurality of detector modules 20 (e.g., detector elements or sensors), and data acquisition systems (DAS) 32. The plurality of detector modules 20 detect the projected X-rays that pass through a subject or object 22 being imaged, and DAS 32 converts the data into digital signals for subsequent processing. Each detector module 20 in a conventional system produces an analog electrical signal that represents the intensity of an incident X-ray beam and hence the attenuated beam as it passes through the subject or object 22. During a scan to acquire X-ray projection data, gantry 12 and the components mounted thereon rotate about a center of rotation 25 (e.g., isocenter) so as to collect attenuation data from a plurality of view angles relative to the imaged volume.

Rotation of gantry 12 and the operation of X-ray source 14 are governed by a control system 26 of CT imaging system 10. Control system 26 includes an X-ray controller 28 that provides power and timing signals to an X-ray source 14, a collimator controller 29 that controls a length and a width of an aperture of the pre-patient collimator 13 (and, thus, the size and shape of the beam of X-rays (e.g., x-ray beam) 16), and a gantry motor controller 30 that controls the rotational speed and position of gantry 12. An image reconstructor 34 receives sampled and digitized X-ray data from DAS 32 and performs high-speed image reconstruction. The reconstructed image is applied as an input to a computer 36, which stores the image in a storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, collimator controller 29, and gantry motor controller 30. In addition, computer 36 operates a table motor controller 44, which controls a motorized table 46 to position subject 22 and gantry 12. Particularly, table 46 moves portions of subject 22 through a gantry opening or bore 48.

FIG. 3 depicts a current version of a post-patient collimator assembly 300 including a collimator 302 and a scintillator 304. The example current post-patient collimator assembly 300 includes a collimator 302 consisting of a plurality of collimator plates 306. The example plates may be made of tungsten. Alternatively, another radiation-blocking material may be used. The collimator plates 306 are depicted as being positioned at a plurality of angles such that a row of the plurality of tungsten plates forms a curved collimator 302, corresponding to, for example, a curve of the gantry of the CT imaging system 10, which enables each beam 16 of X-ray radiation to travel approximately the same distance from the X-ray source 14 to the collimator 302. In alternative examples, such as for use in a standard X-ray detector the collimator plates 306 may be positioned parallel to one another such that the plurality of collimator plates 306 forms a row that is perpendicular to the X-ray source 14.

The example post-patient collimator assembly 300 of FIG. 3 also includes the scintillator 304. The example scintillator 304 includes a plurality of scintillator elements or pixels 308 arranged such that each scintillator element 308 is positioned between two of the plurality of collimator plates 306 in the collimator 302. The scintillator elements or pixels 308 may be made of a ceramic material. In the illustrated example, the scintillator elements 308 are at least partially encased in an epoxy 310 to hold the scintillator elements or pixels 308 in place. The scintillator elements or pixels 308 are positioned parallel to one another, forming a straight row in the scintillator 302. In the illustrated example, the epoxy 310 covers the top and sides of each scintillator element or pixel 308.

An optical coupler 312 and photodiode 314 are attached to bottom surfaces of the plurality of scintillator elements 308. The example optical coupler 312 may operate as a light collimator to improve light collection efficiency of the photodiode 314. The optical coupler 312 may be attached to the scintillator elements 308 via an adhesive and/or the epoxy 310. The example photodiode 314 receives the light energy from the scintillator 302 via the optical coupler 312 and generates a corresponding electrical signal. The electrical signal is then provided to the DAS 32 for image reconstruction.

FIGS. 4A-4G depict a process of manufacturing a post-patient collimator assembly 400 as described herein. The manufacturing process of the example collimator assembly begins with the production of a scintillator pixel or element 402. The example compact pixel or element 402 may be in the form of a compact powder of, for example, a ceramic material. The compact powder may be compressed into a truncated conical shape or truncated pyramidal shape to form a single pixel element or pixel 402. In some examples, the compact powder pixel or element 402 may be made in a mold or using a press. In alternative examples, the scintillator pixel or element 402 is produced using additive manufacturing (e.g., 3-D printing) form a ceramic powder and/or resin powder.

Additionally, the manufacturing process of the example collimator includes the production of an additively manufactured collimator array 404. The example collimator array 404 includes a plurality of cavities or apertures 406 having a truncated conical shape or truncated pyramidal shape corresponding to the shape of the example scintillator element or pixel 402 The shape of the cavities 406 results in tapered cavities in the collimator array 404. The example collimator array 404 is made of tungsten. Alternatively, other materials capable of blocking X-ray radiation may be used instead. The example collimator array 404 is preferably additively manufactured (e.g., 3-D printed), however any sufficient means of producing the example collimator array 404 may be used. In some examples, the example collimator array 404 and scintillator pixels 402 may be additively manufactured in tandem, either separately or together (i.e., each pixel is additively manufactured within a corresponding cavity simultaneously with the additive manufacture of the collimator array). The truncated conical shape or truncated pyramidal shape of the example pixel 402 and cavity 406 of the collimator array 404 increases focal alignment of the X-ray radiation beams to provide optimized collimation (i.e., the cavities 406 and/or pixels 402 of the collimator assembly are focally aligned.

Figures 4A, 4B, 4C, 4D, 4E, 4F, 4G:
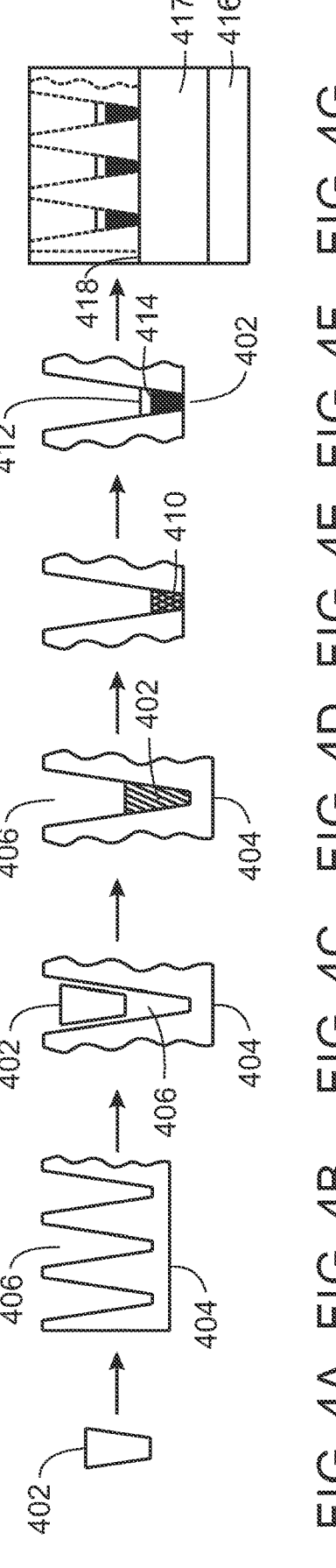
FIGS. 4A-4G depict a process of manufacturing a post-patient collimator assembly as described herein.

FIG. 4C depicts the process of inserting one of the example scintillator pixels 402 in one of the cavities 406 of the scintillator array 404. The process of inserting the example scintillator pixel 402 in the cavity 406 of the collimator array 404 occurs if the example scintillator pixel 402 are manufactured separately (i.e., not as a whole component). In examples where the scintillator pixels 402 and the collimator array 404 are additively manufactured in a single piece or whole component (e.g., using a 3-D printer capable of printing with multiple materials simultaneously), the process depicted in FIG. 4C is not necessary. Alternatively, in some example methods of manufacturing, the process of inserting the example pixel 402 includes pouring a liquid ceramic material in a formed cavity 406 of the collimator array 404. In such examples, the manufacturing process does not include the step of forming the pixel, but instead includes a step of mixing a liquid ceramic material.

FIG. 4D depicts the process of melting or hardening the ceramic and/or resin powder of the example scintillator pixel 402 using a sintering process or hot isostatic press. Melting or hardening the scintillator pixel 402 in place within the cavity 406 of the collimator array corms an inseparable component including both e collimator and scintillator intermeshed in a single component rather stacked on top of one another, such as the prior art post-collimator assembly depicted in FIG. 3.

FIG. 4E depicts the process of grinding down a bottom layer 408 of the collimator assembly 404 to expose the bottom 410 of the scintillator pixel 402, thereby allowing the X-ray radiation to pass completely through the pixel 402. Any sufficient means of griding down the tungsten material of the collimator array 404 may be used to grind down the bottom layer 408 of the collimator array.

FIG. 4F depicts the addition of a reflective material or coating 412 added to a top surface 414 of the scintillator pixel 402. The reflective material allows light to pass through in a first direction (e.g., down through the pixel 402), while preventing light from passing through the second direction (e.g., up away from the pixel 402). The reflective material helps focus the light emitted by the pixel 402 from the bottom surface 410. In some examples, the reflective material may be a film adhered to the top surface 414 of the pixel 402. In some examples, the reflective material is a plate adhered to the top surface 414 of the pixel. In some examples, the reflective material is an epoxy filled with reflective pigments (e.g., a reflective epoxy).

FIG. 4G depicts the final step of manufacturing the example post-patient collimator assembly 400 described herein. In the example final step, a photodiode 416 is attached to the bottom surface of the pixels 402 and a bottom surface 418 of the ground-down collimator array 404. In some examples, an optical coupler 417 may be positioned between the bottom surface 418 and the photodiode 416. The example photodiode 416 may be attached via an adhesive, epoxy, or other suitable means. Manufacturing a post-patient collimator assembly 400 in this manner reduces alignment errors that would typically occur when scintillator pixels is positioned adjacent a scintillator array, as shown in FIG. 3. Thus, this manufacturing process produces a more efficient post-patient collimator assembly 400.

FIG. 5 depicts a cross-sectional side view of the example post-patient collimator assembly 400 depicted in FIGS. 4A-4G, FIG. 6 depicts a top view of the example post-patient collimator assembly 400, and FIG. 7 depicts a bottom view of the example post-patient collimator assembly 400. As depicted in FIG. 5, the plurality of conical or pyramidal cavities 406 are not only a truncated conical shape or truncated pyramidal shape, but walls 502 extending between the cavities may be angled at a variety of angles to help focus the X-ray beam. For example, walls 502 closer to a center of the post-patient collimator assembly 400 may be positioned at an angle essentially perpendicular (e.g., 90 degrees) to the photodiode 416. Walls 502 positioned closer to edges 504 of the post-patient collimator assembly 400 may be positioned at an angle that is further from being perpendicular (e.g., less than 90 degrees, greater than 90 degrees) the further away from center the wall 502 is positioned. While FIG. 5 depicts a post-patient collimator assembly 400 including six pixels 402 in the cross-section, any number of pixels may be used in the post-patient collimator assembly 400. Furthermore, an example CT imaging system 10 may include one or more of the example post-patient collimator assemblies 400 arranged adjacent each other in a row, a column, and or/a plurality of rows and columns, forming a detector array.

FIG. 6 and FIG. 7 depict top and bottom views, respectively, of the example post-patient collimator assembly 400. The top and bottom views each depict a grid-like arrangement of the pixels 402 withing the cavities 402. In the illustrated example, a grid including nine pixels 402 is depicted, but the example post-patient collimator assembly 40 may include a different number of pixels depending on the size of the CT imaging system, the desired size of the detector, the number of other post-patient collimator assemblies 402 combined to form the detector, and/or manufacturing constraints on the size of the post-patient collimator assembly that can be produced using the example methods described herein.

As shown in the top view of the post-patient collimator assembly of FIG. 6, a top surface 602 of the example pixels 402 and/or the reflective material is smaller than an opening 604 of the cavities 406. FIG. 7 depicts the bottom surface of the example post-collimator assembly 702 without the photodiode 416 attached. The bottom surface of the pixels 402 is exposed. FIGS. 6 and 7 depict cavities 406 and pixels 402 having a truncated pyramidal shape, as indicated by the square top surface 602, opening 604, and bottom surface 606. Alternatively, the top surface, opening, and bottom surface may have a circular shape when the pixels 402 and cavities 406 are truncated conical shapes.

FIG. 8 an example method 800 of manufacturing the post-patient collimator depicted in FIGS. 4A-7. The example method 800 begins by producing a collimator with tapered cavities or apertures using a process, such as additive manufacturing (step 802). As discussed above, the tapered openings may have a tapered conical or tapered pyramidal shape. In step 804, a pixel is produced from powered resin or ceramic material. The example pixel has a shape corresponding to the shape of the cavity of the collimator. In some examples, the pixel is produced using an additive manufacturing process in tandem with the example collimator, either separately or together as a single piece of component. In some examples, the method 800 continues in step 806 by positioning the pixel within the cavity. Step 806 is only needed when the pixel is produced separately from the collimator. The pixel is then hardened or melted within the cavity in step 808. The step 808 may include sintering, a hot isostatic press, or any other suitable means of melting or hardening the material of the pixel in the cavity. The method continues with step 810 including griding away a bottom layer of the collimator to expose the bottom of the pixel, which may be done using any means capable of griding the material of the collimator. Finally, a reflective coating is added to a top surface of the pixel. The reflective coating may be applied using an adhesive, or may be an epoxy having reflective pigments that is hardened in the top surface of the pixel (step 812). Additionally, in some examples, the method may include a step of attaching a photodiode to a bottom surface using, for example, an adhesive or any other suitable means of adhering a photodiode to the scintillator and collimator (step 814). The method 800 is complete.

FIGS. 1-7 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example.

As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of manufacturing a post-patient collimator comprising:
   additively manufacturing a collimator array having a plurality of tapered cavities;
   positioning a plurality of scintillator pixels within the collimator array, wherein each of the plurality of scintillator pixels is positioned in one of the cavities of tapered cavities; and
   hardening the plurality of scintillator pixels within the tapered cavities.

2. The method of claim 1, further comprising producing a compact pixel using additive manufacturing.

3. The method of claim 1, wherein positioning a plurality of pixels within the collimator array includes additively manufacturing each of the scintillator pixels within each of the plurality of tapered cavities.

4. The method of claim 1, further comprising grinding down a bottom layer of the collimator array to expose a bottom surface of the scintillator pixels.

5. The method of claim 1, further comprising applying a reflective coating to a top layer of each of the scintillator pixels.

6. The method of claim 5, wherein the reflective coating is a reflective or pigment filled epoxy.

7. The method of claim 5, wherein the reflective coating is adhered to the top layer of each of the scintillator pixels.

8. The method of claim 1, wherein the collimator array is additively manufactured using tungsten.

9. The method of claim 1, wherein each scintillator pixel is a compact powdered ceramic material.

10. The method of claim 1, wherein each scintillator pixel is additively manufactured using ceramic material.

11. The method of claim 1, wherein positioning the plurality of scintillator pixels includes pouring a liquid ceramic material into the plurality of tapered cavities.

12. The method of claim 1, wherein hardening the plurality of scintillator pixels includes sintering.

13. The method of claim 1, wherein hardening the plurality of scintillator pixels includes hot isostatic pressing.

14. A post-patient collimator for x-ray radiation, the post-patient collimator comprising:

a collimator array including a plurality of cavities, wherein each of the plurality of cavities includes tapered walls, and wherein the collimator array is additively manufactured;

a scintillator including a plurality of pixels, each of the plurality of pixels positioned with one of the plurality of cavities of the collimator array; and a reflector positioned on a top of each of the plurality of pixels.

15. The post-patient collimator of claim 14, wherein the collimator array is additively manufactured using tungsten.

16. The post-patient collimator of claim 14, wherein the plurality of pixels are additively manufactured using ceramic.

17. The post-patient collimator of claim 14, wherein the tapered walls of each of the plurality of cavities form a truncated conical cavity in which each pixel is positioned.

18. The post-patient collimator of claim 14, wherein the tapered walls of the plurality of cavities are focally aligned.

19. The post-patient collimator of claim 14, wherein the reflector is a reflective or pigment filled epoxy.

* * * * *